(12) United States Patent
Lee

(10) Patent No.: US 10,207,080 B2
(45) Date of Patent: Feb. 19, 2019

(54) CATHETER APPARATUS FOR CRANIAL CAVITY

(71) Applicant: Je Bum Lee, Bucheon-si (KR)

(72) Inventor: Je Bum Lee, Bucheon-si (KR)

( * ) Notice: Subject to any disclaimer, the term of this patent is extended or adjusted under 35 U.S.C. 154(b) by 75 days.

(21) Appl. No.: 15/170,866

(22) Filed: Jun. 1, 2016

(65) Prior Publication Data

US 2016/0303351 A1 Oct. 20, 2016

(30) Foreign Application Priority Data

Apr. 20, 2015 (KR) .................. 10-2016-0047999
Jun. 5, 2015 (KR) .................. 10-2015-0080050

(51) Int. Cl.
| | | |
|---|---|---|
| A61M 3/00 | (2006.01) | |
| A61M 25/02 | (2006.01) | |
| A61M 25/00 | (2006.01) | |
| A61M 25/01 | (2006.01) | |

(52) U.S. Cl.
CPC ........ *A61M 25/02* (2013.01); *A61M 25/0026* (2013.01); *A61M 25/0194* (2013.01); *A61M 2025/0197* (2013.01); *A61M 2025/024* (2013.01); *A61M 2210/0687* (2013.01); *A61M 2210/0693* (2013.01)

(58) Field of Classification Search
CPC .... A61M 2025/0197; A61M 2025/024; A61M 2210/0687; A61M 2210/0693; A61M 25/0026; A61M 25/0194; A61M 25/02; A61M 25/0097; A61M 27/006; A61M 39/02
See application file for complete search history.

(56) References Cited

U.S. PATENT DOCUMENTS

| | | | | |
|---|---|---|---|---|
| 5,108,364 | A * | 4/1992 | Takezawa ........... | A61M 1/0084 600/549 |
| 5,531,719 | A * | 7/1996 | Takahashi ......... | A61M 25/0045 604/525 |
| 2009/0157006 | A1* | 6/2009 | Nardeo ............. | A61M 25/0662 604/167.03 |
| 2017/0319831 | A1* | 11/2017 | Gill ..................... | A61M 27/006 |

FOREIGN PATENT DOCUMENTS

KR 100178113 B1 4/1999

* cited by examiner

*Primary Examiner* — Rebecca E Eisenberg

(57) ABSTRACT

Disclosed herein is a catheter apparatus for cranial cavities which exhibits the advantage of a conventional catheter structure in that a medicine and a bodily fluid are transferred along different paths, uniformizes the outer diameter of a catheter to easily use stereotactic equipment, and facilitates tunneling of the rear end of the catheter in a bypass space between the skull and the skin, so as to allow an operation to be simply and easily performed and thus to increase safety in operation. The catheter apparatus is advantageous in that no protrusion is formed on the outer surface of the catheter and thus the end of the catheter may be easily and accurately located in a cerebral ventricle using the stereotactic equipment, the catheter may be easily bent through the bypass space, and the rear end of the catheter may be easily exposed to the outside through a perforated part.

8 Claims, 8 Drawing Sheets

CATHETER APPARATUS FOR CRANIAL CAVITY

BACKGROUND OF THE INVENTION

Field of the Invention

The present invention relates to a catheter apparatus for cranial cavities and, more particularly, to a catheter apparatus for cranial cavities which exhibits the advantage of a conventional catheter structure in that a medicine and a bodily fluid are transferred along different paths, uniformizes the outer diameter of a catheter so as to easily use stereotactic equipment to accurately locate the end of the catheter in a cerebral ventricle, and facilitates tunneling of the rear end of the catheter in a bypass space between the skull and the skin, so as to allow an operation to be simply and easily performed and thus to increase safety in operation.

Description of the Related Art

As is well known, hematomas within cerebral ventricles have conventionally been removed together with treatment of diseases through craniotomy which is a neurosurgical operation. However, an operation, in which a catheter is inserted directly into a cerebral ventricle using brain computed tomography or brain magnetic resonance imaging or is more safely and accurately located in a cerebral ventricle using stereotactic equipment and then, a hematoma is removed or cerebrospinal fluid is discharged, is being generalized now.

Such an operation may be executed under local anesthesia within a short time and is thus suitable for a patient sensitive to general anesthesia. For example, in the case of intracerebral hemorrhage, the accurate position of a hematoma within a cerebral ventricle is measured through brain computed tomography, skull drilling is carried out, a catheter is inserted directly into the cerebral ventricle or inserted into the cerebral ventricle using stereotactic equipment, and thereby the hematoma is drained from the cranial cavity. In this case, since the extracranial drainage pattern of the hematoma varies according to the maturity of the hematoma (solid or liquid) and the hematoma should be gradually drained little by little rather than drainage of the entire hematoma at once, the catheter is fixed to the head for a designated period (2 days to 3 weeks or more) so that the remaining hematoma is gradually drained to the outside through the catheter.

Particularly, in the case of a solid hematoma, lysis of the hematoma is carried out by inserting a thrombolytic agent, such as urokinase, through a catheter so that the hematoma can be easily drained, and then the hematoma is drained.

However, since such a conventional catheter apparatus has one drain pipe serving as a single fluid path, when it is necessary to inject a thrombolytic agent, an antibiotic or a saline solution, a considerable amount of a bodily fluid, such as a hematoma or a cerebrospinal fluid, filling the inside of the catheter should be introduced again into the brain and the saline solution of an amount corresponding to the inner volume of the catheter should be additionally injected, and thus, the conventional catheter apparatus causes increased intracranial pressure, the risk of infection due to repeated injection and cumbersomeness in manipulation.

Therefore, in order to solve these problems, a catheter 12 shown in FIG. 2 has been developed. FIG. 2 illustrates the catheter 12 disclosed in Korean Patent Registration No. 0178113.

In more detail, as exemplarily shown in FIG. 1, in order to drain and remove a bodily fluid including a hematoma or a cerebrospinal fluid within a cerebral ventricle 9, a skull 6 located vertically above the cerebral ventricle 9 is accurately measured and is drilled along the line A.

A cranial cavity refers to a space including a brain 4 within the skull 6, and, after drilling of the skull 6 along the line A, the catheter 12 disclosed in Korean Patent Registration No. 0178113 is inserted into a hole formed by drilling the skull 6 such that one end of the catheter 12 is located at an affected part 10, i.e., in the cerebral ventricle 9.

In this case, the other end of the catheter 12 may not be located just above the end of the catheter 12 inserted into the affected part 10 in order to prevent infection and, as exemplarily shown in FIG. 1, the catheter 12 is configured such that the other end of the catheter 12 is bent from the end of the catheter 12 inserted into the affected part 10. Therefore, an electrical needle is connected to the other end of the catheter 12, and the other end of the catheter 12 is bent and passes through a bypass space 8 formed between a skin 2 and the upper surface of the skull 6 by drilling and is extruded to the outside through another pierced portion of the skin 2. Such a technique is referred to as subcutaneous tissue tunneling.

That is, the other end of the catheter 12 is not exposed from a position just above the hole of the cerebral ventricle 9 but is exposed from a position bent from the hole of the cerebral ventricle 9 through the bypass space 8.

The exposed catheter 12 may be fixed by a separate fixture 19. Here, the catheter 12 passes through a through hole 21 formed in a body 23 of the fixture 19 and the body 23 is fixed to the skull 6 or the skin through separate fixing units passing through fixing holes 25.

A drain pipe 14 to drain a bodily fluid including a hematoma or a cerebrospinal fluid to the outside is formed at the center of the catheter 12 and a medicine transfer pipe 18 is formed at a designated region at the outside of the drain pipe 14.

A designated portion of one end of the medicine transfer pipe 18 is incised and connected to a medicine injection pipe 22, and the medicine transfer pipe 18 and the medicine injection pipe 22 are firmly connected to each other by a connection member 24.

Therefore, the bodily fluid including the hematoma or the cerebrospinal fluid, introduced from the affected part 10 through drain holes 16 is drained to the outside through the drain pipe 14 and, when a syringe (not shown) is coupled with the medicine injection pipe 22 and injects a thrombolytic agent, an antibiotic or a saline solution, the injected thrombolytic agent, antibiotic or saline solution is discharged from a medicine discharge hole 20 via the medicine injection pipe 22 and the medicine transfer pipe 18 and introduced into the affected part 10.

However, in an operation of inserting such a catheter into the affected part 10, the end of the catheter 12 should be inserted into the cerebral ventricle 9 along an accurate path and, unless the end of the catheter 12 is not inserted into the cerebral ventricle 9 along the accurate path, the catheter 12 may damage brain tissue around the path and thus a high degree of skill is required. In order to prevent such a mistake, stereotactic equipment (not shown) is used and, for this purpose, the catheter 12 should be configured so as to have no protrusion at the outer portion thereof.

However, the catheter 12 is configured such that the medicine injection pipe 22 is connected to the medicine transfer pipe 18 through the separate connection member 24 and thus the medicine injection pipe 22 branched from a connection region into a Y shape protrudes from the outer surface of the catheter 12. Therefore, it is difficult to use stereotactic equipment and to perform tunneling of the rear end of the catheter 12 between the skull 6 and the skin 2, thus causing difficulty and complexity in operation.

SUMMARY OF THE INVENTION

Therefore, the present invention has been made in view of the above problems, and it is an object of the present invention to provide a catheter apparatus for cranial cavities which exhibits the advantage of a conventional catheter structure in that a medicine and a bodily fluid are transferred along different paths, uniformizes the outer diameter of a catheter so as to easily use stereotactic equipment to accurately locate the end of the catheter in the cerebral ventricle, and facilitates tunneling of the rear end of the catheter in a bypass space between the skull and the skin, so as to allow an operation to be simply and easily performed and thus to increase safety in operation.

In accordance with the present invention, the above and other objects can be accomplished by the provision of a catheter apparatus for cranial cavities, including a catheter including a drain pipe formed at the center thereof to discharge a hematoma or a bodily fluid including a cerebrospinal fluid to the outside, a plurality of drain holes formed at the front end of the drain pipe, a medicine transfer pipe formed at a designated region at the outside of the drain pipe, the rear end of the medicine transfer pipe being closed with a finishing member so that, after the catheter is installed within a cerebral ventricle, a plastic pipe is inserted into a designated portion of the medicine transfer pipe so as to inject a medicine, and a binding member configured to fix the plastic pipe and an extension tube without separation under the condition that the extension tube is coupled with the plastic pipe.

A hole may be formed through a designated portion of the rear end of the medicine transfer pipe so that the plastic pipe may be inserted into the hole, and a temporary closing packing may be inserted into the hole so as to temporarily close the hole.

The plastic pipe may be a pipe formed of a synthetic resin so as to be gently bent at a connection portion thereof to the medicine transfer pipe and be covered with a silicon tube so as not to be broken, and the other end of the plastic pipe may be provided with a Luer connector and a swabable valve or a heparin cap.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, preferred embodiments of the present invention will be described with reference to the annexed drawings.

Figure 1:
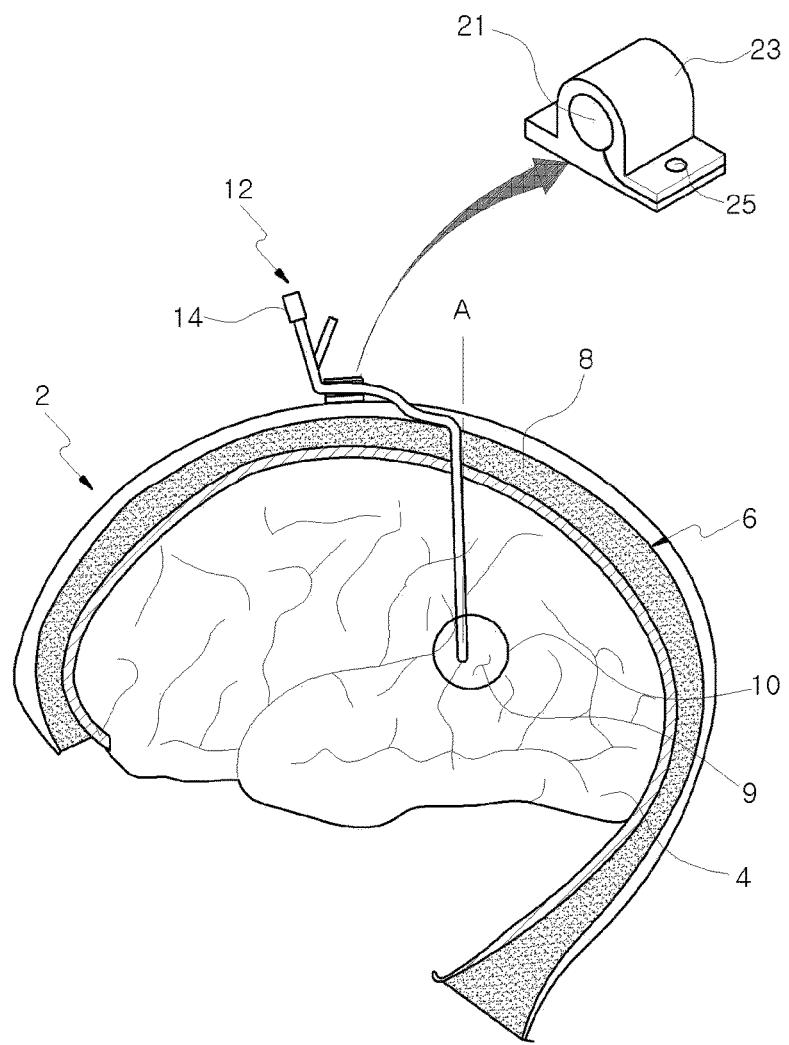
FIG. 1 is a cross-sectional view illustrating an operation state using a conventional catheter for cranial cavities.
Figure 2:
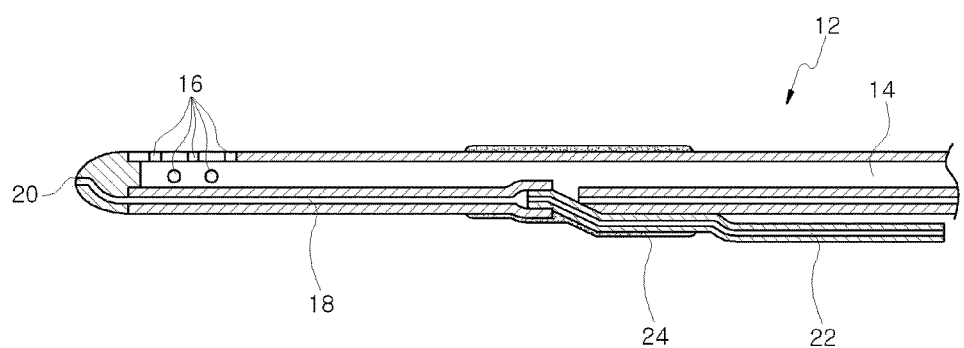
FIG. 2 is a cross-sectional view illustrating the conventional catheter for cranial cavities.
Figure 3:
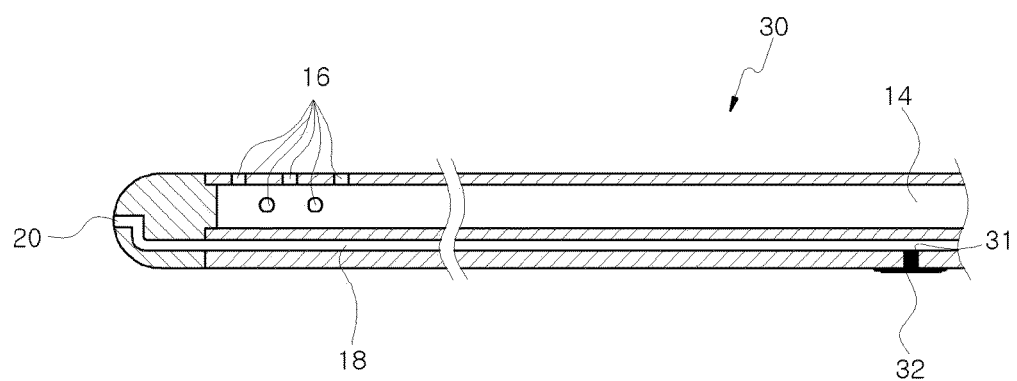
FIG. 3 is a cross-sectional view illustrating a catheter for cranial cavities in accordance with one embodiment of the present invention.
Figure 4:
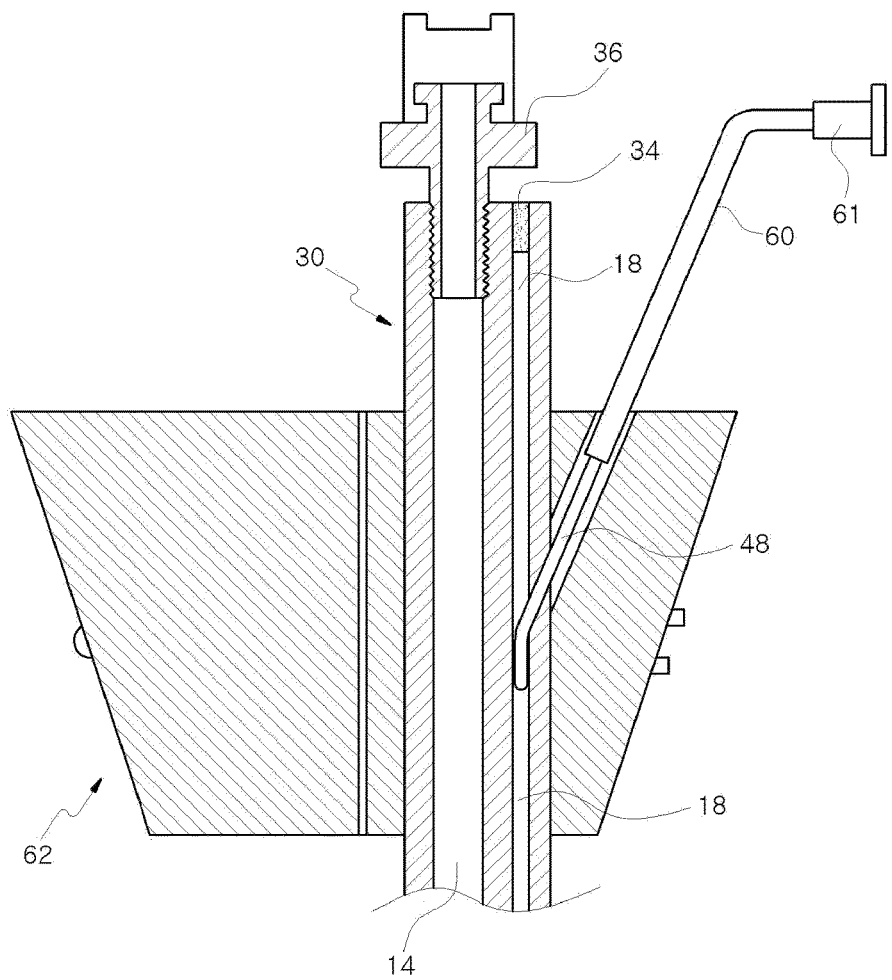
FIG. 4 is a cross-sectional view illustrating the catheter for cranial cavities in accordance with the embodiment of the present invention which is provided with a binding member.
Figure 5:
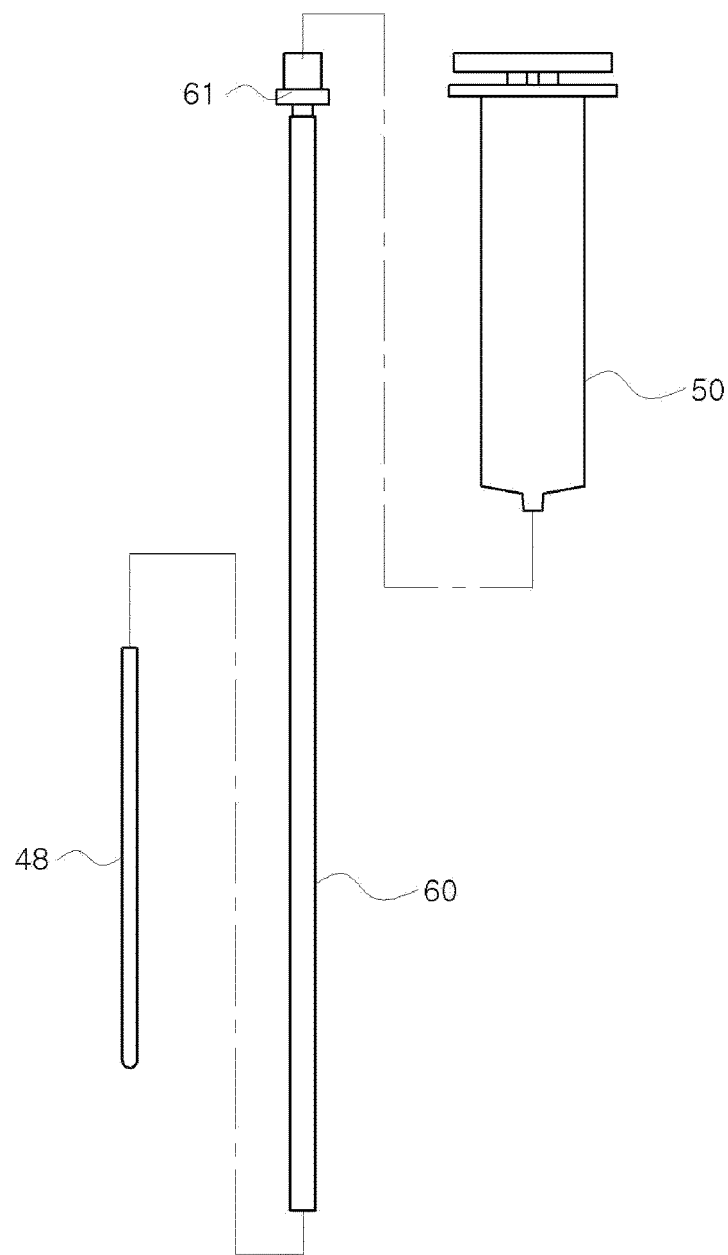
FIG. 5 is a view illustrating a connection state among a plastic pipe, an extension tube and a syringe.
Figure 6A:
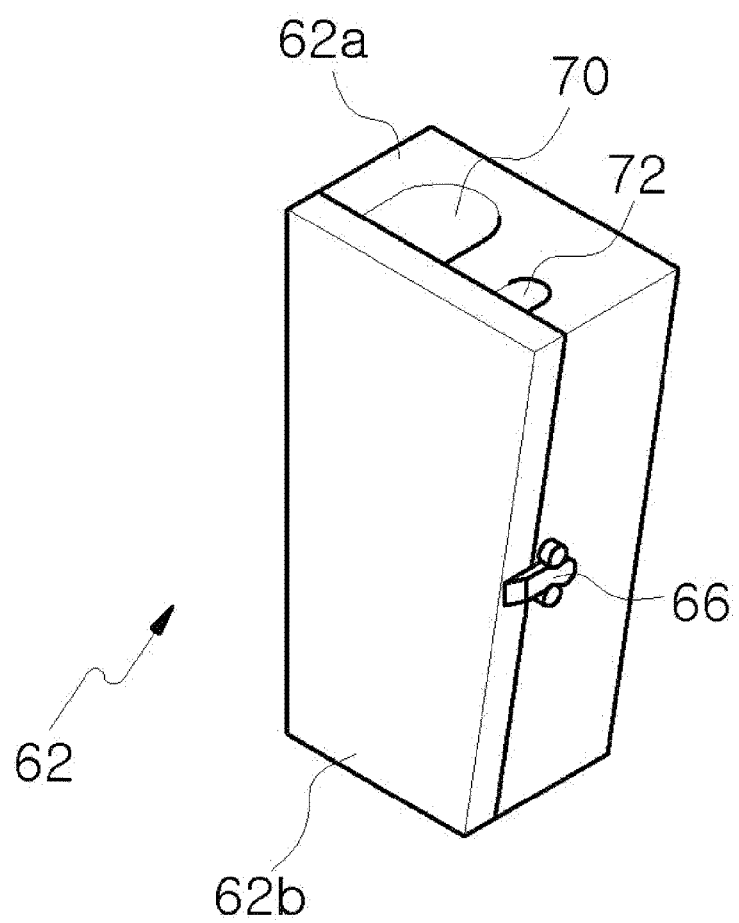
FIGS. 6A, 6B and 6C are perspective views illustrating a connection state of the binding member of FIG. 4.
Figure 6B:
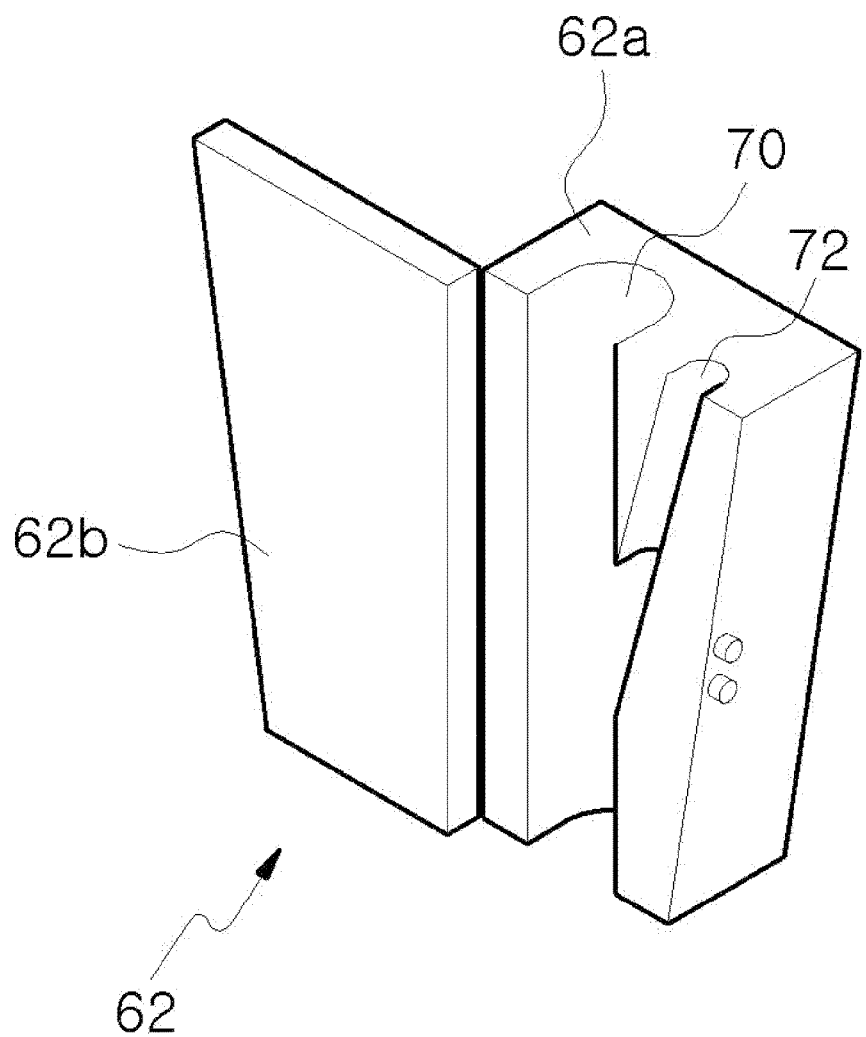
Figure 6C:
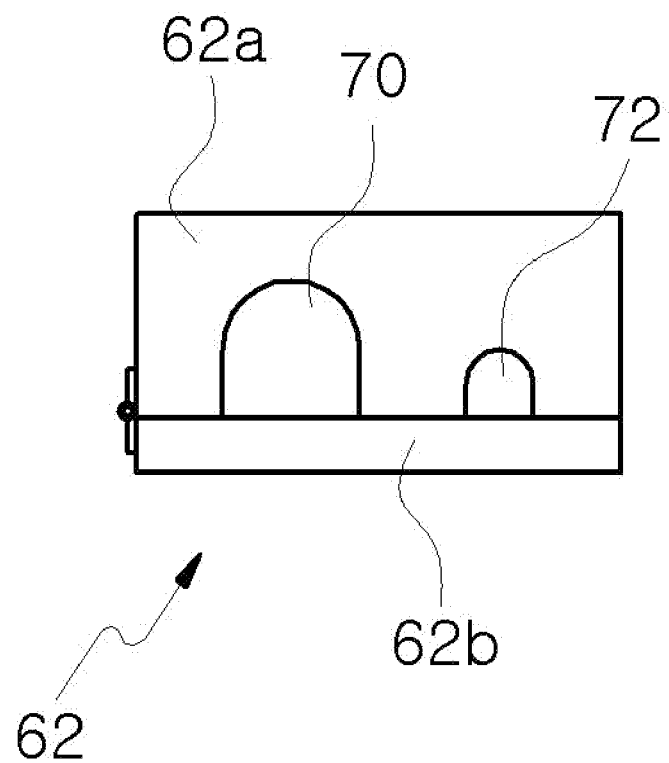

FIG. 3 is a cross-sectional view illustrating a catheter for cranial cavities in accordance with one embodiment of the present invention, FIG. 4 is a cross-sectional view illustrating the catheter for cranial cavities in accordance with the embodiment of the present invention which is provided with a binding member, FIG. 5 is a view illustrating a connection state among a plastic pipe, an extension tube and a syringe, and FIGS. 6A, 6B and 6C are perspective views illustrating a connection state of the binding member of FIG. 4.

With reference to FIGS. 3 to 6C, a catheter apparatus for cranial cavities in accordance with one embodiment of the present invention exhibits the advantage of a conventional catheter structure in that a medicine and a bodily fluid are transferred along different paths, uniformizes the outer diameter of a catheter so as to easily use stereotactic equipment to accurately locate the end of the catheter in a cerebral ventricle, and facilitates subcutaneous tissue tunneling of the rear end of the catheter in a bypass space between the skull and the skin, thereby allowing an operation to be simply and easily performed and thus increasing safety in operation.

In more detail, the catheter apparatus for cranial cavities in accordance with one embodiment of the present invention includes a catheter for cranial cavities 30, a plastic pipe 48, an extension tube 60, and a binding member 62.

A drain pipe 14 to drain a bodily fluid including a hematoma or a cerebrospinal fluid to the outside is formed at the center of the catheter for cranial cavities 30, a plurality of drain holes 16 is formed at the front end of the drain pipe 14, a medicine transfer pipe 18 is formed at a designated region at the outside of the drain pipe 14, and the rear end of the medicine transfer pipe 18 is closed with a finishing member 34. Through such a configuration, after the catheter for cranial cavities 30 is installed within a cerebral ventricle, the plastic pipe 48 is inserted into a designated portion of the catheter for cranial cavities 30 so as to inject a medicine.

A binding member 62 is provided to fix the catheter for cranial cavities 30, the plastic pipe 48 and the extension tube 60 without separation under the condition that the extension tube 60 is coupled with the plastic pipe 48.

That is, the drain pipe 14 has a greater diameter than the medicine transfer pipe 18 and drains a bodily fluid including a hematoma or a cerebrospinal fluid to the outside, and a separate bodily fluid storage bag (not shown) is coupled with the rear end of the drain pipe 14 via a connector 36.

Further, the plastic pipe 48 is a pipe formed of a synthetic resin so as to be gently bent at a connection portion thereof to the medicine transfer pipe 18 and is covered with a silicon tube so as not to be broken, and the other end of the plastic pipe 48 is provided with a Luer connector 61 and a swabable valve or a heparin cap.

The medicine transfer pipe 18 has a smaller diameter than the drain pipe 14 and serves to inject a medicine, such as a thrombolytic agent, an antibiotic or a saline solution, into a cranial cavity from the outside of the cranial cavity. The medicine transfer pipe 18 is not branched off into a separate Y-shaped pipe and uniformizes the outer diameter of the catheter for cranial cavities 30, thereby facilitating usage of stereotactic equipment, facilitating subcutaneous tissue tunneling using an electronic needle and thus allowing the catheter for cranial cavities 30 to be easily bent during operation.

An insertion hole 31 is formed through a designated portion of the rear end of the medicine transfer pipe 18 so that the plastic pipe 48 may be inserted into the insertion hole 31, and a temporary closing packing 32 temporarily closes the insertion hole 31.

That is, in the catheter for cranial cavities 30 in accordance with one embodiment of the present invention, since the insertion hole 31 into which the plastic pipe 48 may be inserted is formed through the designated portion of the rear end of the medicine transfer pipe 18 and the temporary closing packing 32 temporarily closes the insertion hole 31, when, during operation, the temporary closing packing 32 is removed and the plastic pipe 48 is inserted into the medicine transfer pipe 18 through the insertion hole 31, an insertion process is completed and, thus, an operator does not need to pay attention not to accidently pierce the drain pipe 14 adjacent to the medicine transfer pipe 18 by mistake.

Further, the plastic pipe 48 is a pipe formed of a synthetic resin so as to be bent at a designated angle within the medicine transfer pipe 18 and is covered with a silicon tube so as to prevent the plastic pipe 48 from being broken and to uniformize the insertion depth of the plastic pipe 48.

That is, the plastic pipe 48 is a pipe formed of a synthetic resin.

Here, the plastic pipe 48 is in a flexible state and, thus, if the plastic pipe 48 is obliquely inserted into the medicine transfer pipe 18 when the plastic pipe 48 is introduced into the medicine transfer pipe 18, the plastic pipe 48 is easily introduced into the medicine transfer pipe 18.

Further, the catheter apparatus for cranial cavities in accordance with one embodiment of the present invention further includes the binding member 62 provided to allow an operation to be carried out under the condition that the plastic pipe 48, the extension tube 60 and the catheter for cranial cavities 30 are more firmly combined.

Here, the Luer connector 61 is provided at the end of the extension tube 60.

Further, the binding member 62 is configured such that first and second bodies 62a and 62b are rotated about a hinge so as to be coupled with each other or separated from each other under the condition that the first and second bodies 62a and 62b are opposite each other, and the second body 62b is a planar panel serving as a cover of the first body 62a.

Within the first body 62a, a first insertion hole 70, through which the catheter for cranial cavities 30 passes, is formed to pass through the upper and lower surfaces of the first body 62a and a second insertion hole 72, into which the plastic pipe 48 and the extension tube 60 are inserted, is formed.

The first and second insertion holes 70 and 72 are formed into a Y shape such that the plastic pipe 48 and the extension tube 60 may be introduced into the catheter for cranial cavities 30, inserted into the first insertion hole 70, through the second insertion hole 72, as exemplarily shown in FIGS. 6A, 6B and 6C.

The extension tube 60 may be formed of silicon.

A locking unit 66 to interconnect the first and second bodies 62a and 62b so as to lock the first and second bodies 62a and 62b with each other or to release locking between the first and second bodies 62a and 62b may be further provided on the first and second bodies 62a and 62b.

That is, the hinge (not shown) may be formed on one surface of the binding member 62 and the locking unit 66 may be formed on another surface of the binding member 62 opposite the hinge, so that the side surfaces of the first and second bodies 62a and 62b provided with the first and second insertion holes 70 and 72 are opened from each other or closed to each other.

Consequently, in the catheter apparatus for cranial cavities in accordance with one embodiment of the present invention, since the catheter 30, the plastic tube 48 and the extension tube 60 are integrally combined within the binding member 62 under the condition that the Luer connector 61 and the swabable valve or the heparin cap are connected to the extension tube 60, no additional assistant operator is required.

The catheter apparatus for cranial cavities in accordance with the embodiment of the present invention is not limited to the above-described embodiment and those skilled in the art will appreciate that various modifications, additions and substitutions are possible, without departing from the scope and spirit of the invention as disclosed in the accompanying claims.

As apparent from the above description, a catheter apparatus for cranial cavities in accordance with the present invention is advantageous in that no protrusion is formed on the outer surface of a catheter and thus the end of the catheter may be easily and accurately located in a cerebral ventricle using stereotactic equipment, the catheter may be easily guided to be bent through a bypass space between the upper part of the skull and the skin, and the rear end of the catheter may be easily exposed to the outside of a cranial cavity through a perforated part.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A catheter apparatus for cranial cavities, comprising:
a catheter including a drain pipe formed at the center thereof to drain a bodily fluid including a hematoma or a cerebrospinal fluid to the outside, a plurality of drain holes formed at the front end of the drain pipe, a medicine transfer pipe formed at a designated region at the outside of the drain pipe, the rear end of the medicine transfer pipe being closed with a finishing member so that, after the catheter is installed within a cerebral ventricle, a plastic pipe is inserted into a designated portion of the medicine transfer pipe so as to inject a medicine; and
a binding member configured to fix the plastic pipe and an extension tube without separation under the condition that the extension tube is coupled with the plastic pipe wherein the binding member is configured such that first and second bodies are rotated about a hinge so as to be coupled with each other or separated from each other under the condition that the first and second bodies are opposite each other, the second body is a planar panel serving as a cover of the first body, a first insertion hole to pass the catheter is formed to pass through the upper and lower surfaces of the first body, a second insertion hole to receive the plastic pipe and the extension tube is formed within the first body, and the first and second insertion holes respectively pass the catheter and the plastic pipe.

2. The catheter apparatus for cranial cavities according to claim 1, wherein a hole is formed through a designated portion of the rear end of the medicine transfer pipe so that the plastic pipe may be inserted into the hole, and a temporary closing packing is inserted into the hole so as to temporarily close the hole.

3. The catheter apparatus for cranial cavities according to claim 1, wherein the plastic pipe is a pipe formed of a synthetic resin so as to be gently bent at a connection portion thereof to the medicine transfer pipe and is covered with a silicon tube so as not to be broken, and the other end of the plastic pipe is provided with a Luer connector and a swabable valve or a heparin cap.

4. The catheter apparatus for cranial cavities according to claim 1, wherein the hinge is provided on one surface of the binding member and a locking unit including a hanging loop and a hanging holder is provided on another surface of the binding member opposite the hinge so as to interconnect the first and second bodies.

5. A catheter apparatus for cranial cavities, comprising:
a catheter including a drain pipe inside the catheter, the drain pipe having a plurality of drain holes at distal portion, the catheter having a medicine transfer pipe inside the catheter, the catheter having a catheter insertion hole formed through the medicine transfer pipe;
an extension tube having a plastic pipe coupled with the extension tube; and
a binding member having a first body and a second body wherein the binding member is configured such that first and second bodies are rotated about a hinge so as to be coupled with each other or separated from each other under the condition that the first and second bodies are opposite each other, the second body is a planar panel serving as a cover of the first body, the first body comprising a first insertion hole and a second insertion hole, the first insertion hole configured to pass the catheter, the second insertion hole configured to pass the extension tube, the first and second holes formed into a Y-shape within the first body such that the plastic pipe coupled with the extension tube is introduced into the catheter insertion hole and inserted into the first insertion hole through the second insertion hole.

6. The catheter apparatus for cranial cavities according to claim 5, wherein a hole is formed through a designated proximal portion of the medicine transfer pipe so that the plastic pipe may be inserted into the hole, and a temporary closing packing is inserted into the hole so as to temporarily close the hole.

7. The catheter apparatus for cranial cavities according to claim 5, wherein the plastic pipe is a pipe formed of a synthetic resin so as to be gently bent at a connection portion thereof to the medicine transfer pipe and is covered with a silicon tube so as not to be broken, and the other end of the plastic pipe is provided with a Luer connector and a swabable valve or a heparin cap.

8. The catheter apparatus for cranial cavities according to claim 5 wherein the hinge is provided on one surface of the binding member and a locking unit including a hanging loop and a hanging holder is provided on another surface of the binding member opposite the hinge so as to interconnect the first and second bodies.

* * * * *